(12) United States Patent
Hu et al.

(10) Patent No.: US 10,624,278 B2
(45) Date of Patent: Apr. 21, 2020

(54) **CULTIVATION METHOD FOR THE RAPID PROPAGATION OF *DAVIDIA INVOLUCRATA* WINTER BUDS**

(71) Applicants: Mianyang Teachers' College, Mianyang (CN); Mianyang Shuchuang Agricultural Technology Co., Ltd., Mianyang (CN)

(72) Inventors: Jinyao Hu, Mianyang (CN); Lijuan Zou, Mianyang (CN); Li Xiang, Mianyang (CN)

(73) Assignees: MIANYANG TEACHERS' COLLEGE, Mianyang (CN); MIANYANG SHUCHUANG AGRICULTURAL TECHNOLOGY CO., LTD., Mianyang (CN)

( * ) Notice: Subject to any disclaimer, the term of this patent is extended or adjusted under 35 U.S.C. 154(b) by 226 days.

(21) Appl. No.: 15/921,672

(22) Filed: Mar. 15, 2018

(65) Prior Publication Data
US 2019/0059247 A1 Feb. 28, 2019

(30) Foreign Application Priority Data
Aug. 30, 2017 (CN) .......................... 2017 1 0765844

(51) Int. Cl.
| | | |
|---|---|---|
| *A01G 7/06* | (2006.01) | |
| *A01G 22/60* | (2018.01) | |
| *A01N 43/90* | (2006.01) | |
| *A01N 45/00* | (2006.01) | |
| *A01N 25/22* | (2006.01) | |

(Continued)

(52) U.S. Cl.
CPC .............. *A01G 22/60* (2018.02); *A01G 2/00* (2018.02); *A01G 7/045* (2013.01); *A01G 7/06* (2013.01); *A01G 24/28* (2018.02); *A01N 25/22* (2013.01); *A01N 35/02* (2013.01); *A01N 37/10* (2013.01); *A01N 43/38* (2013.01); *A01N 43/90* (2013.01); *A01N 45/00* (2013.01); *A01N 47/18* (2013.01); *A01N 59/00* (2013.01); *A01N 59/16* (2013.01); *A01N 59/20* (2013.01); *A61L 2/0088* (2013.01); *A61L 2/07* (2013.01); *C05G 3/00* (2013.01); *A01G 9/14* (2013.01); *A01G 9/20* (2013.01); *A61L 2202/17* (2013.01)

(58) Field of Classification Search
CPC ............... A01G 2/00; A01G 7/00; A01G 7/06
USPC .......................... 47/58.1 R, 58.1 SC, 58.1 SE
See application file for complete search history.

(56) References Cited

U.S. PATENT DOCUMENTS

| | | | | |
|---|---|---|---|---|
| 2006/0101549 P1 * | 5/2006 | Shibamichi | ............... | A01H 5/12 Plt./216 |
| 2006/0101550 P1 * | 5/2006 | Shibamichi | ............... | A01H 5/00 Plt./216 |

FOREIGN PATENT DOCUMENTS

| | | | |
|---|---|---|---|
| JP | 6-237658 | * | 8/1994 |
| WO | WO 2010/068777 | * | 6/2010 |

* cited by examiner

*Primary Examiner* — David J Parsley
(74) *Attorney, Agent, or Firm* — Bayramoglu Law Offices LLC (57) ABSTRACT

The present invention discloses a cultivation method for the rapid propagation of *Davidia involucrata* winter buds. The method includes the following steps: (1) collecting winter buds of *Davidia involucrata* as explants; (2) disinfecting and sterilizing; (3) primary culture of the winter buds; (4) propagation cultivating; (5) cultivating of the strong seedlings; (6) cultivating roots; (7) acclimatization and transplanting; (8) water and fertilizer management. The method (Continued)

of the present invention can effectively promote the artificial propagation of *Davidia involucrata* and improve the survival rate thereof.

8 Claims, 2 Drawing Sheets

(51) Int. Cl.
*A01N 43/38* (2006.01)
*C05G 3/00* (2020.01)
*A01N 59/20* (2006.01)
*A01N 35/02* (2006.01)
*A01N 59/16* (2006.01)
*A01N 47/18* (2006.01)
*A61L 2/00* (2006.01)
*A01G 2/00* (2018.01)
*A01G 7/04* (2006.01)
*A01G 24/28* (2018.01)
*A01N 37/10* (2006.01)
*A61L 2/07* (2006.01)
*A01N 59/00* (2006.01)
*A01G 9/20* (2006.01)
*A01G 9/14* (2006.01)

CULTIVATION METHOD FOR THE RAPID PROPAGATION OF *DAVIDIA INVOLUCRATA* WINTER BUDS

CROSS REFERENCE TO RELATED APPLICATIONS

This application is based upon and claims priority to Chinese Patent Application No. CN2017107658449, filed on Aug. 30, 2017, the entire content of which is incorporated herein by reference.

TECHNICAL FIELD

The present invention relates to a technical field of *Davidia involucrata* cultivation, specially relates to a cultivation method for the rapid propagation of *Davidia involucrata* winter buds.

BACKGROUND

*Davidia involucrata* is a deciduous tree. The *Davidia involucrata* may grow to 20-25 m in height. The leaves thereof are broad ovate shaped with serration on the edge. The flowers of the *Davidia involucrata* are very beautiful. The *Davidia involucrata* is a relict plant of the Tertiary Period of the Cenozoic Era ten million years ago, which got extinct in most areas during the Quaternary glaciation. *Davidia involucrata* survived only in some areas in South China and became the living fossil of plant, which is known as the "dove-tree in China", also referred to as "dove-flower tree" and "water pears". The *Davidia involucrata* is native to Sichuan Province in Southwest China, Hubei Province in middle-China and surrounding areas. Therefore, The *Davidia involucrata* is listed as the Class I protected wild plant by the national government of China. The *Davidia involucrata* is endemic to China and is a relict plant, as well as a world's famous ornamental plants and a Class I protected plant in China.

As the wild *Davidia involucrata* only exists in Sichuan Province in Southwest China, Hubei Province in middle-China and surrounding areas, there are only a few number of wild plants. Therefore, it is necessary to establish a cultivation method for the artificial rapid propagation to cultivate the *Davidia involucrata*, achieving the purpose of protection and commercialization.

SUMMARY

In view of the drawbacks in the prior art mentioned above, the present invention provides a cultivation method for the rapid propagation of *Davidia involucrata* winter buds to solve the problem of slow artificial propagation of *Davidia involucrata*.

The technical solutions of the present invention to solve the technical problems are as follows: a cultivation method for the rapid propagation of *Davidia involucrata* winter buds, includes:

(1) Collecting a plurality of winter buds without germination of 1 to 2-year-old *Davidia involucrata* as a plurality of explants;

(2) Disinfecting and sterilizing;

immersing the plurality of winter buds into a detergent solution with a concentration of 3-5 g/mL for 2-3 minutes, pruning the plurality of winter buds to a plurality of bud ends of 0.3-0.5 cm in height, immersing the plurality of bud ends in a 75% ethanol for 10-30 seconds, then immersing in a 0.01% mercuric chloride solution for 1-7 minutes; or, immersing the bud ends in the 0.01% mercuric chloride solution for 1-8 minutes only;

(3) Primary culture of the winter buds;

adding NAA, 6-BA, $GA_3$ and AC into a WPM medium, adjusting a pH value of the medium to 5.8-6.0, sterilizing at 120-125° C. for 20-25 minutes, cooling to room temperature for further application; inoculating the plurality of sterilized winter buds in step (2) into the medium, incubating at a temperature of 24±1° C. and illuminating for 8-10 hours per day at 2000-2100 1× until the plurality of winter buds budding into a plurality of stems with buds; wherein an addition amount of the NAA is 0-0.4 mg/L, an addition amount of the 6-BA is 2.0-4.0 mg/L, an addition amount of the $GA_3$ is 0-2.0 mg/L, and an addition amount of the AC is 1.0-1.5 g/L;

(4) Propagation cultivating;

inoculating the products obtained in step (3) into the WPM medium containing NAA, 6-BA and AC, incubating at the temperature of 24±1° C. and illuminating for 8-10 hours per day at 2000-2100 1× for propagation cultivation to obtain a plurality of *Davidia involucrata* saplings; wherein the addition amount of the NAA is 0.2-0.6 mg/L, the addition amount of the 6-BA is 1.0-4.0 mg/L, and the addition amount of the AC is 0.5-1.5 g/L;

(5) Cultivating of the strong seedlings;

inoculating the plurality of *Davidia involucrata* saplings obtained in step (4) in the WPM medium containing NAA, 6-BA, $GA_3$ and AC at the temperature of 24±1° C. and illuminating for 8-10 hours per day at 2000-2100 1× to cultivate the plurality of *Davidia involucrata* saplings obtained in step (4), wherein; the addition amount of the NAA is 0.5-1.5 mg/L, the addition amount of the 6-BA is 0.2-1.0 mg/L, the addition amount of the $GA_3$ is 0.5-1.5 mg/L and the addition amount of the AC is 0.5-1.5 g/L;

(6) Cultivating Roots;

selecting a plurality of *Davidia involucrata* saplings in good condition obtained in step (5) to cultivate in a White medium containing IBA, 6-BA and AC at the temperature of 24±1° C. and illuminating for 8-10 hours per day at 2000-2100 1× until roots are cultivated; wherein an addition amount of the IBA is 2.0-4.0 mg/L, the addition amount of the 6-BA is 0-1.5 mg/L and the addition amount of the AC is 0.5-1.5 g/L;

(7) Acclimatization and transplanting;

closed-tank acclimatizing the plurality of *Davidia involucrata* saplings for 15-20 days with a shading degree of 50%-70% after 7-15 days of the root cultivation, open-tank acclimatizing the plurality of *Davidia involucrata* saplings for 3-7 days, then emigrating the plurality of *Davidia involucrata* saplings, disinfecting and sterilizing, transplanting into a disinfectant substrate, pouring a sufficient amount of water and spray a nutrient solution every 5 days; wherein the substrate is a mixture of peat, perlite and vermiculite, and a mass ratio of the peat, perlite and vermiculite is 1-2:0.5-1:0.5-1;

(8) Applying a normal water and fertilizer management after the transplantation, cultivating to obtain a plurality of *Davidia involucrata* plantlets.

Preferably, in the WPM medium of step (3), the addition amount of the NAA is 0.3 mg/L, the addition amount of the 6-BA is 2.0 mg/L, the addition amount of the $GA_3$ is 2.0 mg/L, and the addition amount of the AC is 1.5 g/L.

Preferably, in the WPM medium of step (4), the addition amount of the NAA is 0.4 mg/L, the addition amount of the 6-BA is 4.0 mg/L and the addition amount of the AC is 1.5 g/L.

Preferably, in the WPM medium for the cultivation of the strong seedlings in step (5), the addition amount of the NAA is 1.0 mg/L, the addition amount of the 6-BA is 1.0 mg/L, the addition amount of the $GA_3$ is 1.0 mg/L and the addition amount of the AC is 1.0 g/L.

Preferably, in the White medium for rooting cultivation in step (6), the addition amount of the IBA is 3.0 mg/L, the addition amount of the 6-BA is 1.0 mg/L and the addition amount of the AC is 1.0 g/L.

Preferably, the mass ratio of the peat, perlite and vermiculite in step (7) is 2:1:1.

Preferably, a disinfecting progress of the substrate in step (7) is as follows:

placing the substrate into a 0.1 MPa autoclave for 20-30 minutes; or soaking the substrate with a 5% formalin or a 0.3% copper sulfate solution and then covering for 7 days using a plastic sheet.

Preferably, a disinfection process of the *Davidia involucrata* saplings in step (7) is as follows:

washing the *Davidia involucrata* saplings with a 0.1%-0.3% potassium permanganate solution or a 500 times carbendazim solution.

The beneficial effects of the present invention are as follows:

1. As there is a thick bud scale protection outside the winter buds, when the winter buds are disinfected by the conventional method, there is a problem that the unthorough disinfection will lead to the infection of bacteria in the tissue culture process. Therefore, the winter buds of *Davidia involucrata* are seldom used in the tissue culture propagation. Hence, when disinfecting and sterilizing the winter buds, the method of the present invention uses a detergent solution with a concentration of 3-5 g/mL to immerse firstly to remove the impurities including the earth, and then treats with a 75% ethanol and a 0.01% mercuric chloride solution. The disinfecting is convenient and less damaging to the buds.

2. Use of the medium with a pH value of 5.8-6.0 and performing the primary culture of the winter buds at 2000-2100 1× can promote the rapid germination of winter buds to stems with buds and breaks dormancy. What's more, under this condition, the winter buds have a largest amount of germination and maximum germination efficiency.

3. Under the premise of the maximum germination efficiency and the largest amount of germination, the proliferation medium reduces the gibberellin in the components and adjusts the ratio of the corresponding components according to the composition and ratio of medium used in the primary culture of the winter buds. The growth of the budding stems of the winter buds are promoted under the premise of ensuring the maximum proliferation efficiency, improving the survival rate of *Davidia involucrata* saplings.

4. As the *Davidia involucrata* saplings can be obtained after the cultivation of the proliferation medium, when selecting the components of the strong seedling medium, compared to the components of the proliferation medium, gibberellin is added and the ratio of all the components is adjusted to maximize the effect of strong seedlings.

5. Using the acclimatizing method in the present invention can make the survival rate of the *Davidia involucrata* saplings more than 80%.

6. The present invention uses the winter buds as explants to establish a complete set of rapid propagation technology system of tissue culture of *Davidia involucrata*, which effectively solves the problems of winter buds in the process of disinfection, proliferation, rooting and acclimatizing and can cultivate a lot of *Davidia involucrata* saplings in a short time. And, the acclimatizing technology is matured with a survival rate of up to 80%.

DETAILED DESCRIPTION OF THE INVENTION

The principle and features of the present invention are described below with reference to the embodiments. The embodiments are used only to explain the present invention, and are not intended to limit the scope of the present invention. The specific conditions which are not specified in the embodiments are processed according to the normal conditions or the conditions suggested by the manufacturer. Reagents or instruments used which are not specified by the manufacturers are conventional products available through the commercial purchase.

Embodiment 1

A cultivation method for the rapid propagation of *Davidia involucrata* winter buds including the following steps:

(1) collecting a plurality of winter buds without germination of 1 to 2-year-old *Davidia involucrata* as a plurality of explants;

(2) disinfecting and sterilizing;

disinfecting and sterilizing of the winter buds: immersing the plurality of winter buds collected in the field into a detergent solution with a concentration of 3-5 g/mL for 2 minutes, gently cleaning the bud scales using a soft brush, rinsing for 2 hours with running water, and then immersing the winter buds using the 0.1% mercuric chloride solution for 20 minutes on a clean bench, rinsing with sterile water for more than 5 times, blotting up the water on the surface of the explants with sterile filter paper, stripping up all the scales of the winter buds using a tweezer to obtain the buds, treating with 75% ethanol and mercuric chloride solution or treating with mercuric chloride solution only. Wherein each treatment is inoculated into 30 bottles and 2 explants in each bottle. The specific progress is as follows:

a. disinfecting and sterilizing using 75% ethanol and 0.01% mercuric chloride solution (See Table 1)

Cutting off all bright yellow velvet leaves on the bud, preserving bud ends of only 0.5 cm in height, disinfecting the surface with 75% ethanol for 10-30 seconds, removing the buds, and then washing with sterile water for 2-5 times, and then immersing the buds with 0.01% mercuric chloride solution for 1-7 min, blotting up the water on the surface of the buds with sterile filter paper. The disinfecting results are shown in Table 2.

TABLE 1 disinfecting and sterilizing using 75% ethanol in
combination with 0.01% mercuric chloride solution

| | disinfector | |
|---|---|---|
| Disposal | 75% ethanol (s) | 0.01% mercuric chloride solution (min) |
| ① | 10 | 1 |
| ② | 15 | 3 |
| ③ | 20 | 5 |
| ④ | 30 | 7 |

TABLE 2 disinfecting results using methods of Table 1

| | Disposal | | | |
|---|---|---|---|---|
| | ① | ② | ③ | ④ |
| Pollution rate (%) | 31.8 | 25.2 | 14.0 | 10.0 |
| Death rate (%) | 0 | 4 | 6 | 56 | b、Disinfecting and Sterilizing Using 0.01% Mercuric Chloride Solution 0.01% (See Table 3)

immersing the buds in 0.01% mercuric chloride solution for 4-8 minutes, removing the buds, blotting up the water using sterile filter paper, the treatment results are shown in Table 4.

TABLE 3 disinfecting and sterilizing using 0.01% mercuric chloride solution

| | Disposal (0.01% mercuric chloride solution) | | | | |
|---|---|---|---|---|---|
| | ① | ② | ③ | ④ | ⑤ |
| Treating time (min) | 4 | 5 | 6 | 7 | 8 |

TABLE 4 disinfecting results using methods of Table 3

| | Disposal | | | | |
|---|---|---|---|---|---|
| | ① | ② | ③ | ④ | ⑤ |
| Pollution rate (%) | 38 | 27.2 | 18 | 16 | 10 |
| Death rate (%) | 3 | 5 | 6 | 36 | 45 |

It can be seen from the results of Table 2 and Table 4 that the pollution rate is inversely proportional to the death rate, which may be due to the different degrees of killing effect of the different disinfection treatments to cells: the shorter the disinfection time is, the less is the degree of cell killing, therefore, the corresponding pollution rate is high and the death rate is relatively low. The longer the disinfection time is, the greater is the degree of cell killing, the corresponding pollution rate is low and the death rate is high. It can be seen that the third disinfection method in Table 1 is the best, that is, firstly immersing in 75% alcohol for 20 seconds, and then immersing in 0.01% mercuric chloride solution for 5 minutes. This method is the optimum condition for disinfection of the winter buds.

(3) primary culture of the winter buds;

Establishing 11 groups of WPM mediums containing different amounts of NAA and 6-BA (See Table 3), adding 1.5 g/L AC into each group of the WPM medium, adjusting the pH values to 5.8-6.0, autoclaving at 121° C. for 20 minutes, cooling to room temperature; inoculating the plurality of disinfected winter buds in step (2) into No. 1, 4, 5, 6, 7, 8, 9, 10 and 11 mediums with 3 repeats, wherein each medium contains 10 bottles and 3 explants in each bottle; after the incubation, incubating at a temperature of 24±1° C. and illuminating for 10 hours per day at 2000-2100 1x until the plurality of winter buds budding into a plurality of stems with buds; calculating the germination rate of the winter buds 75 days later. The results are shown in Table 6.

TABLE 5 mediums for primary culture of the winter buds

No. of WPM basic culture medium

1 NAA 0 mg/L + 6-BA 2.0 mg/L
2 NAA 0 mg/L + 6-BA 2.0 mg/L + LH 300 mg/L
3 NAA 0.05 mg/L + 6-BA 2.0 mg/L
4 NAA 2.0 mg/L + 6-BA 2.0 mg/L
5 NAA 0.3 mg/L + 6-BA 2.0 mg/L + LH 300 mg/L
6 NAA 0.3 mg/L + 6-BA 2.0 mg/L + $GA_3$ 2.0 mg/L
7 NAA 0.3 mg/L + 6-BA 3.0 mg/L
8 NAA 0.3 mg/L + 6-BA 4.0 mg/L
9 NAA 0.4 mg/L + 6-BA 2.0 mg/L
10 NAA 0.4 mg/L + 6-BA 3.0 mg/L
11 NAA 0.4 mg/L + 6-BA 4.0 mg/L

TABLE 6 effects of the primary culture mediums on the germination of the winter buds

Figure 1:
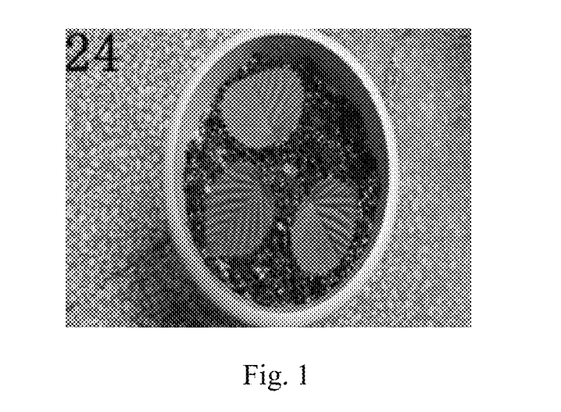
FIG. 1 is a growth diagram of winter buds after the primary culture.

| No. of the medium | starting time (day) | The number of buds | Growth status |
|---|---|---|---|
| 1 | 65a | 4a | A few calluses on the base; leaves are fully expanded and the margins of the leaves are red, the leaves are dark green; budding slowly. |
| 4 | 75c | 1c | It takes only 5 days for expansion of leaves, but only the expansion of leaves; budding very slowly. |
| 5 | 37b | 13b | Leaves are fully expanded, the leaves are dark green; a part of the buds budding stems with buds, the stems are thick and strong; budding quickly. |
| 6 | 36b | 20b | The leaves expand largely (See FIG. 1), the leaves are light green with uneven distribution in color; a part of the buds budding stems with buds, but the stems are slender; budding quickly. |
| 7 | 54a | 7a | Leaves are fully expanded, the leaves are dark green; new leaves grow slowly. |
| 8 | 30b | 16b | A few calluses on the base; the leaves are dark green; a part of the buds budding stems with buds; budding quickly. |
| 9 | 52a | 4a | Grow quickly, the margins of the leaves are red, budding relatively quick. |
| 10 | 60a | 7a | A few calluses on the base; the leaves are dark green; budding relatively quick. |
| 11 | 33b | 19b | A few calluses on the base; the leaves are dark green; a part of the buds budding stems with buds, the stems are thick and strong; budding quickly. |

Note:
no significant difference between the same letters (p > 0.05)

Figure 2:
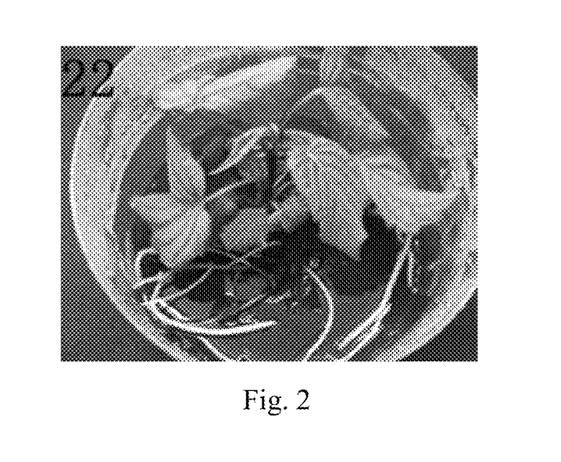
FIG. 2 and FIG. 3 are both the growth diagrams of inducing the winter buds to generate the stems.
Figure 3:
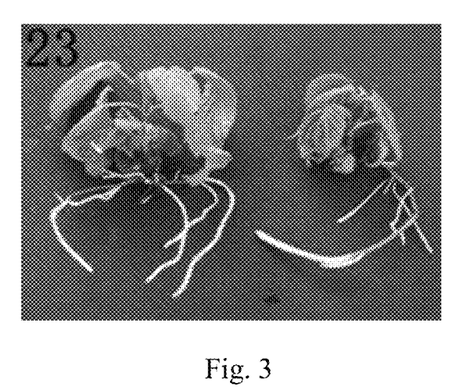

According to the results in Table 6, except for the No. 4 medium, the induction rate of the germination of the winter buds of other mediums reached 100%, that is, there was growth of new leaves. In addition, the type and concentration of the hormone had a significant effect on the germination of *Davidia involucrata* winter buds. There were significant differences (p<0.01) on the start time of budding and the amount of buds with stem segments between the 9 kinds of mediums. The germination time of No. 5, 6, 8 and 11 mediums were the shortest with most buds; the germination time and the amount of buds thereof have a significant difference (P<0.01) compared with those of the other mediums. Further, there is no significant difference between the four groups of No. 5, 6, 8 and 11 mediums. The buds bud fast in these mediums and grew quickly and there were stems with grown buds (See FIG. 2 and FIG. 3), which provided material for a further propagation of the stems. The start time of budding and the amount of stems with buds of No. 1, 6, 7, 9 and 10 mediums were second to those of No. 5, 6, 8 and 11 mediums, and there is no significant difference between the five mediums. The No. 4 medium took the longest time to start budding and had the least stems with buds, which has a significant difference (p<0.05) compared to the other mediums. The buds grew slowly in No. 4 medium and most buds died over time. A comprehensive comparison of the budding and growth state indicates that the No. 5, 6, 8 and 11 mediums can be used as the appropriate mediums for the germination of the winter buds of the *Davidia involucrata* into stems with buds. Due to the addition of gibberellin, the buds in the No. 6 medium grew fastest and most vigorously. Therefore, the optimal medium is: WPM+NAA 0.3 mg/L+ 6-BA 2.0 mg/L+GA$_3$2.0 mg/L+AC 1.5 g/L. Wherein the activated carbon (1.5%) was added to the mediums to prevent browning.

(4) Propagation cultivating;

inoculating the products obtained in step (3) into the No. 2-3 and 5-11 mediums with 3 repeats, wherein each medium contains 10 bottles and 3 explants in each bottle; incubating in the culture chamber at the temperature of 24±1° C. and illuminating for 10 hours per day at 2000 1× for propagation cultivation of the cluster buds to obtain a plurality of *Davidia involucrata* saplings; calculating the growth results 60 days later (See Table 7).

TABLE 7

Effect of different combinations of hormones on the direct induction of the cluster buds of *D. involucrata* winter buds

| No. of the medium | Inducing percentage (%) | The number of buds | Growth status |
| --- | --- | --- | --- |
| 2 | 20f | 1.2f | A few buds proliferated to sole scion in a good state. |
| 3 | 47e | 2.5e | The buds proliferated well, the cluster buds were thick and strong, but the buds grew slowly. |
| 5 | 40ef | 3.0ef | The buds proliferated well, the cluster buds were thick and strong, the buds grew well but slowly. |
| 6 | 73ab | 3.6bc | The buds proliferated well, there were many cluster buds, the buds grew well and fast. |
| 7 | 50cde | 2.8de | The buds proliferated well, the cluster buds were slender, grew slowly. |
| 8 | 67bcd | 3.1bcd | The buds proliferated well, the cluster buds were very slender, the buds grew very fast. |
| 9 | 50cde | 1.8e | A few buds proliferated, the cluster buds were thick and strong, the buds grew relatively slowly. |
| 10 | 68bc | 3.8ab | The buds proliferated well, the cluster buds grew well and fast |
| 11 | 87a | 4.0a | The buds proliferated well, there were many cluster buds, thick and strong, grew well and fast. |

Wherein, firstly, the rate of bud induction (%)=the number of explants that differentiated into cluster buds/(the number of inoculated explants–the number of contaminated explants)×100%; the average number of new buds=the total number of cluster buds/the number of explants that differentiated into cluster buds.

Secondly, numbers are followed by one or more same letters, representing no significant difference exists between the data (p>0.05).

Figure 4:
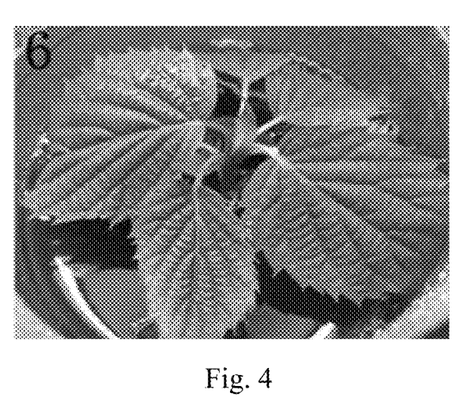
FIG. 4 is the *Davidia involucrata* saplings obtained after the propagation cultivation of the winter buds.

One-way analysis of variance multiple comparison method (LSD) is used. It can be seen from Table 7 that, the nine mediums tested can be used to directly induce the winter buds to generate the cluster buds. The lactalbumin hydrolysate (LH) was beneficial for the proliferation and growth of the cluster buds in the absence or low concentration of NAA. The results of analysis showed that the induction rate of cluster buds from the *Davidia involucrata* winter buds of the No. 11 medium was the highest, which has no significant difference (p=0.061) compared to that of the No. 6 medium and has a significant difference with other mediums (p<0.05). The average amount of the new buds of direct induction of cluster buds on the No. 11 medium is maximum, and has no significant difference (p=0.132) compared to that of the No. 10 medium, and has a significant difference with other mediums (p<0.05). A comprehensive comparison showed that the No. 11 medium is the optimal medium for the germination of the winter buds of the *Davidia involucrata* into stems with buds, the specific ingredient thereof is: WPM+NAA 0.4 mg/L+6-BA 4.0 mg/L+AC 1.5 g/L. The highest induction ratio in the medium is 87% where the most cluster buds (4.0) and the buds were thick and strong (See FIG. 4).

(5) cultivating the strong seedlings;

inoculating the plurality of *Davidia involucrata* saplings obtained in step (4) in nine groups of WPM medium (See Table 8) containing different concentrations of NAA, 6-BA and $GA_3$ at the temperature of $24\pm1°$ C. and illuminating for 10 hours per day at 2000 1× to cultivate the plurality of *Davidia involucrata* saplings obtained in step (4) for 36 days. The amount of AC added for each group of WPM medium is 1.0 g/L. Calculating the average height of the saplings (See Table 9).

TABLE 8

The strong seedling medium

| Groups | $GA_3$ | NAA | 6-BA |
|---|---|---|---|
| 1 | 0.5 | 0.5 | 0.2 |
| 2 | 0.5 | 1.0 | 0.6 |
| 3 | 0.5 | 1.5 | 1.0 |
| 4 | 1.0 | 0.5 | 0.6 |
| 5 | 1.0 | 1.0 | 1.0 |
| 6 | 1.0 | 1.5 | 0.2 |
| 7 | 1.5 | 0.5 | 1.0 |
| 8 | 1.5 | 1.0 | 0.2 |
| 9 | 1.5 | 1.5 | 0.6 |

TABLE 9

The results of the cultivation of the strong seedlings

| Group | factors A($GA_3$) | B(NAA) | C(6-BA) | Average height (cm) |
|---|---|---|---|---|
| 1 | 0.5 | 0.5 | 0.2 | 1.44 |
| 2 | 0.5 | 1.0 | 0.6 | 1.84 |
| 3 | 0.5 | 1.5 | 1.0 | 1.71 |
| 4 | 1.0 | 0.5 | 0.6 | 1.61 |
| 5 | 1.0 | 1.0 | 1.0 | 2.42 |
| 6 | 1.0 | 1.5 | 0.2 | 2.08 |
| 7 | 1.5 | 0.5 | 1.0 | 1.56 |
| 8 | 1.5 | 1.0 | 0.2 | 1.94 |
| 9 | 1.5 | 1.5 | 0.6 | 1.64 |
| K1 | 1.663 | 1.537 | 1.820 | |
| K2 | 2.037 | 2.067 | 1.697 | |
| K3 | 1.713 | 1.810 | 1.897 | |
| R | 0.374 | 0.530 | 0.200 | |

The effects of $GA_3$, NAA and 6-BA on strong seedling culture were studied using rootless seedlings. Table 9 showed that the ranges (R value) of the three factors is B>A>C. Therefore, the effect of the three factors on the average height of seedlings was $GA_3$>NAA>6-BA. At the same time, the analysis of variance showed that $GA_3$ and NAA reached the significant level on the cultivation of the strong seedlings. Therefore, $GA_3$ and NAA were the main factors affecting the average height of the strong seedlings. Therefore, the optimal medium for the cultivation of the strong seedling is: WPM+$GA_3$1.0 mg/L+NAA 1.0 mg/L+6-BA 1.0 mg/L+AC 1.0 g/L. The average height of the *Davidia involucrata* saplings cultivated on the medium can be 2.42 cm.

(6) cultivating roots;

inoculating the plurality of *Davidia involucrata* saplings in good condition obtained in step (5) in the White, WPM and 1/4 MS medium (See Table 10) containing different concentrations of IBA, 6-BA and AC at the temperature of $24\pm1°$ C. and illuminating for 10 hours per day at 2000 1× to cultivate the plurality of *Davidia involucrata* saplings in good condition obtained in step (5) until rooting. Analyzing the rooting results (See Table 11).

TABLE 10

The rooting mediums

| Level | A (minimal medium) | B IBA (mg/L) | C 6-BA (mg/L) | D AC powder (g/L) |
|---|---|---|---|---|
| 1 | ¼MS | 2.0 | 0 | 0.5 |
| 2 | WPM | 3.0 | 1.0 | 1.0 |
| 3 | White | 3.0 | 1.5 | 1.5 |

TABLE 11

Orthogonal experimental results of the rooting cultivation

| Groups | Factors A medium | B (IBA) IBA | C (6-BA) 6-BA | D(C powder) AC | Rooting Ratio (%) |
|---|---|---|---|---|---|
| 1 | ¼MS | 1.0 | 0 | 0.5 | 26.78 |
| 2 | ¼MS | 2.0 | 1.0 | 1.0 | 52.34 |
| 3 | ¼MS | 3.0 | 1.5 | 1.5 | 34.8 |
| 4 | WPM | 1.0 | 1.0 | 1.5 | 65.89 |
| 5 | WPM | 2.0 | 1.5 | 0.5 | 62.33 |
| 6 | WPM | 3.0 | 0 | 1.0 | 45.9 |
| 7 | White | 1.0 | 1.5 | 1.0 | 74.32 |
| 8 | White | 2.0 | 0 | 1.5 | 72.34 |
| 9 | White | 3.0 | 1.0 | 0.5 | 85.49 |
| K1 | 37.973 | 55.663 | 48.340 | 58.200 | |
| K2 | 58.040 | 62.337 | 67.907 | 57.520 | |
| K3 | 77.383 | 55.397 | 57.150 | 57.677 | |
| R | 39.410 | 6.940 | 19.567 | 0.680 | |

Table 11 showed that the ranges (R value) of the four factors are A>C>B>D. Therefore, the effects of the four factors on the average height of seedlings were medium >6-BA>IBA>AC. It can be seen from the rooting ratio in Table 11 that the optimal medium for rooting of the *Davidia involucrata* saplings is the No. 9 medium, the rooting ratio thereof is 85.49%. The specific ingredient thereof is White+IBA 3.0 mg/L+6-BA 1.0 mg/L+AC 0.5 g/L.

(7) acclimatizing and transplanting;

The acclimatization includes a closed-tank acclimatization and open-tank acclimatization, the specific process is as follows:

Closed-tank acclimatization: 7-15 days after the root cultivation, removing the tissue culture tank with the plurality of *Davidia involucrata* saplings into an outdoor shade or a greenhouse, closed-tank acclimatizing for 15-20 days with a shading degree of 50%-70%.

Open-tank acclimatization: opening the cover of the tissue culture tank after the closed-tank acclimatization, open-tank acclimatizing in natural light for 3-7 days; the open-tank acclimatization includes three stages, firstly, loose the cover of the tissue culture tank for 1-2 days, then partially open the tank for 1-2 days, finally fully open the tank for 1-3 days. During the open-tank acclimatization, note to take measurements to prevent the *Davidia involucrata* saplings from being burned due to strong light.

Removing the *Davidia involucrata* saplings from the tissue culture tank using a tweezer, washing the roots of the *Davidia involucrata* saplings to avoid the residual sucrose and nutrients in the roots becoming the medium for the growth of pathogenic microorganisms, which can effectively prevent the *Davidia involucrata* saplings from death induced by root rotting after the transplant.

Then, transplanting directly, or washing the *Davidia involucrata* saplings 2-3 times using a 0.1%43% potassium permanganate solution or a 500 times carbendazim solution, then washing with water, transplanting into four groups of sterilized mediums respectively, pouring a sufficient amount of water and spraying a nutrient solution every 5 days, and paying attention to shading and ventilation. Take every 50 holes of nursery tray as a district, 3 repeats, calculating the survival rate and the average plant height 60 days later.

A mass ratio of each component of the substrate:

(1) a ratio of the pearlite to vermiculite is 1:1; (2) humus soil; (3) a ratio of the peat to perlite is 1:1; (4) a ratio of the turf to pearlite to vermiculite is 2:1:1.

A sterilization process of the substrate:

(1) baking the substrate in an oven at 120° C. for 20 minutes, or holding in a 0.1 MPa autoclaves for 20-30 minutes;

(2) soaking the substrate with a 5% formalin or a 0.3% copper sulfate solution and then covering for 7 days using a plastic sheet, opening the sheet, flipping the substrate to volatilize the smell.

According to the statistical results, the optimal growth substrate for the *Davidia involucrata* saplings is peat, perlite and vermiculite with a ratio of 2:1:1.

(8) management after transplant;

Fertilizing at regular intervals, applying a normal water and fertilizer management after the transplantation, cultivating to obtain a plurality of *Davidia involucrata* plantlets.

The method of the present invention uses the winter buds of *Davidia involucrata* as explants for cultivation, which is convenient to disinfect, and capable of obtaining a large number of *Davidia involucrata* seedlings by cultivation in a short term, and the survival rate can be up to 80%.

The above are only the preferred embodiments of the present invention and not intended to limit the present invention. Any modification, equivalent replacement, improvement, etc. within the spirit and principle of the present invention should be included in the protection scope.

The invention claimed is:

1. A cultivation method for the rapid propagation of *Davidia involucrata* winter buds, comprising the following steps:

(1) collecting a plurality of winter buds without germination of 1 to 2-year-old *Davidia involucrata* as a plurality of explants;

(2) disinfecting and sterilizing;

comprising the sub-steps as follows: immersing the plurality of winter buds into a detergent solution with a concentration of 3-5 g/mL for 2-3 minutes, pruning the plurality of winter buds to a plurality of bud ends of 0.3-0.5 cm in height, immersing the plurality of bud ends in a 75% ethanol for 10-30 seconds, then immersing in a 0.01% mercuric chloride solution for 1-7 minutes; or, immersing the bud ends in the 0.01% mercuric chloride solution for 1-8 minutes only;

(3) primary culture of the winter buds;

comprising the sub-steps as follows: adding NAA, 6-BA, $GA_3$ and AC into a WPM medium, adjusting a pH value of the medium to 5.8-6.0, sterilizing at 120-125° C. for 20-25 minutes, cooling to room temperature for further application; inoculating the plurality of sterilized winter buds in step (2) into the medium, incubating at a temperature of 24±1° C. and illuminating for 8-10 hours per day at 2000-2100 1× until the plurality of winter buds budding into a plurality of stems with buds; wherein an addition amount of the NAA is 0-0.4 mg/L, an addition amount of the 6-BA is 2.0-4.0 mg/L, an addition amount of the $GA_3$ is 0-2.0 mg/L, and an addition amount of the AC is 1.0-1.5 g/L;

(4) propagation cultivating;

comprising the sub-steps as follows: inoculating the products obtained in step (3) into a WPM medium containing NAA, 6-BA and AC, incubating at the temperature of 24±1° C. and illuminating for 8-10 hours per day at 2000-2100 1× for propagation cultivation to obtain a plurality of *Davidia involucrata* saplings; wherein the addition amount of the NAA is 0.2-0.6 mg/L, the addition amount of the 6-BA is 1.0-4.0 mg/L, and the addition amount of the AC is 0.5-1.5 g/L;

(5) cultivating of the seedlings;

comprising the sub-steps as follows: inoculating the plurality of *Davidia involucrata* saplings obtained in step (4) in the WPM medium containing NAA, 6-BA, $GA_3$ and AC at the temperature of 24±1° C. and illuminating for 8-10 hours per day at 2000-2100 1×, wherein; the addition amount of the NAA is 0.5-1.5 mg/L, the addition amount of the 6-BA is 0.2-1.0 mg/L, the addition amount of the $GA_3$ is 0.5-1.5 mg/L and the addition amount of the AC is 0.5-1.5 g/L;

(6) cultivating roots;

comprising the sub-steps as follows: selecting a plurality of *Davidia involucrata* saplings in good condition obtained in step (5) to cultivate in a white medium containing IBA, 6-BA and AC at the temperature of 24±1° C. and illuminating for 8-10 hours per day at 2000-2100 1× until rooting; wherein an addition amount of the IBA is 2.0-4.0 mg/L, the addition amount of the 6-BA is 0-1.5 mg/L and the addition amount of the AC is 0.5-1.5 g/L;

(7) acclimatizing and transplanting;

comprising the sub-steps as follows: closed-tank acclimatizing the plurality of *Davidia involucrata* saplings for 15-20 days with a shading degree of 50%-70% after 7-15 days of the rooting cultivation, open-tank acclimatizing for 3-7 days, then emigrating the plurality of *Davidia involucrata* saplings, disinfecting and sterilizing, transplanting into a disinfectant substrate, pouring a sufficient amount of water and spray a nutrient solution every 5 days; wherein the substrate is a mixture of peat, perlite and vermiculite, and a mass ratio of the peat, perlite and vermiculite is 1-2:0.5-1:0.5-1;

(8) applying a normal water and fertilizer management after the transplantation, cultivating to obtain a plurality of *Davidia involucrata* plantlets.

2. The cultivation method for the rapid propagation of *Davidia involucrata* winter buds according to claim 1, wherein in the WPM medium of step (3), the addition amount of the NAA is 0.3 mg/L, the addition amount of the 6-BA is 2.0 mg/L, the addition amount of the $GA_3$ is 2.0 mg/L, and the addition amount of the AC is 1.5 g/L.

3. The cultivation method for the rapid propagation of *Davidia involucrata* winter buds according to claim 1, wherein in the WPM medium of step (4), the addition amount of the NAA is 0.4 mg/L, the addition amount of the 6-BA is 4.0 mg/L and the addition amount of the AC is 1.5 g/L.

4. The cultivation method for the rapid propagation of *Davidia involucrata* winter buds according to claim 1, wherein in the WPM medium for the cultivation of the seedlings in step (5), the addition amount of the NAA is 1.0 mg/L, the addition amount of the 6-BA is 1.0 mg/L, the addition amount of the $GA_3$ is 1.0 mg/L and the addition amount of the AC is 1.0 g/L.

5. The cultivation method for the rapid propagation of *Davidia involucrata* winter buds according to claim 1, wherein in the White medium for rooting cultivation in step (6), the addition amount of the IBA is 3.0 mg/L, the addition amount of the 6-BA is 1.0 mg/L and the addition amount of the AC is 1.0 g/L.

6. The cultivation method for the rapid propagation of *Davidia involucrata* winter buds according to claim 1, wherein the mass ratio of the peat, perlite and vermiculite in step (7) is 2:1:1.

7. The cultivation method for the rapid propagation of *Davidia involucrata* winter buds according to claim 1, wherein a disinfecting progress of the substrate in step (7) is as follows:
   placing the substrate into a 0.1 MPa autoclave for 20-30 minutes; or soaking the substrate with a 5% formalin or a 0.3% copper sulfate solution and then covering for 7 days using a plastic sheet.

8. The cultivation method for the rapid propagation of *Davidia involucrata* winter buds according to claim 1, wherein the disinfection of the *Davidia involucrata* saplings in step (7) is as follows:
   washing the *Davidia involucrata* saplings for 2-3 times with a 0.1%-0.3% potassium permanganate solution or a 500 times carbendazim solution.

* * * * *